US007290542B1

(12) United States Patent
    Carpin

(10) Patent No.: US 7,290,542 B1
(45) Date of Patent: Nov. 6, 2007

(54) SYSTEM AND METHOD FOR DELIVERING AND METERING POWDER AEROSOL

(75) Inventor: John C. Carpin, Perry Hall, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 609 days.

(21) Appl. No.: 10/989,981

(22) Filed: Nov. 16, 2004

(51) Int. Cl.
    *A61M 11/00* (2006.01)
(52) U.S. Cl. .......................... 128/200.21; 128/200.23; 128/200.14
(58) Field of Classification Search ..............................
        128/200.21–200.23, 200.14, 203.14, 203.25, 128/204.24, 204.25
    See application file for complete search history.

(56) References Cited

U.S. PATENT DOCUMENTS 5,533,498 A * 7/1996 Sioutas .................. 128/200.23
7,059,319 B2 * 6/2006 Ganan-Calvo ......... 128/200.14

* cited by examiner

*Primary Examiner*—Steven O. Douglas
(74) *Attorney, Agent, or Firm*—Ulysses John Biffoni

(57) ABSTRACT

Safe, reliable and controlled dissemination of a powder aerosol over a relatively short period is achieved by infusing the powder aerosol into a holding chamber to form a concentrated powder aerosol cloud, reducing the volume of the holding chamber to exhaust the concentrated powder aerosol at a controlled rate, mixing a gas with the concentrated powder aerosol, and monitoring the admixture of gas and concentrated aerosol to achieve a target concentration.

27 Claims, 3 Drawing Sheets

SYSTEM AND METHOD FOR DELIVERING AND METERING POWDER AEROSOL

GOVERNMENT INTEREST

The invention described herein may be manufactured, licensed, and used by or for the U.S. Government.

TECHNICAL FIELD

The present invention relates in general to devices and systems for delivering powder aerosols, and more particularly to a system and method for delivering and metering of a powder aerosol, such as a highly toxic chemical or biological agent, at a controlled rate for a relatively short period.

BACKGROUND

A "powder" or "dry" aerosol, as used herein, is a relatively stable suspension of fine solid particles in a gas, especially air. There is an increasing need for reliable data on the effects of short term exposure to many toxic chemical, biological and radiological powder aerosols. For example, inhalation toxicology studies are needed to determine the effects of brief exposures to atmospheres containing minute amounts of highly toxic chemical, biological, or radiological threat agents. Such studies present numerous technical challenges and, thus, there is a shortage of useful data on the effects of short term inhalation exposure to many toxic powder aerosols.

It is difficult to achieve a controlled mass flow rate of a powder aerosol. Gravitational, fluid dynamic, and interactive forces, such as electrostatic, van der Waals, and capillary forces, can introduce significant flow rate variations. Electrostatic charge interactions between dry aerosol particles and device surfaces can also disrupt aerosol flows. Additionally, particle size distribution, particle morphology, and moisture content can influence powder aerosol flow rates.

As the toxicity of the test substances increases, exposure periods and concentrations must be controlled with greater precision. Short duration tests of extremely toxic dry aerosols can range from several seconds to 30 minutes or more, and aerosols must often be generated from very small quantities of powder, typically in the range of 25-500 mg. Particles may be less than 1 micron in diameter, can become easily airborne, disseminate rapidly in the air and adhere to a variety of surfaces. Precautions taken in handling and containment of test substances greatly complicate test administration. Simple procedures such as pouring and weighing of powders and the transfer of powder from one vessel to another, become slow and cumbersome to perform and meticulous clean up of the containment facility is necessary after each experiment.

A variety of systems have been used to generate atmospheres containing toxic aerosols. Systems typically incorporate two basic mechanisms. First, a metering device is used to control the flow rate of the powder to be tested. Second, a pneumatic device, such as a high velocity/sonic air jet or a fluidized column of beads, is used to disperse the powder into an air stream which may then, for example, be administered to one or more test subjects in an inhalation toxicology study. Typical metering devices include helical screw feeders, rotary gear feeders, split tube feeders, rotating turntable feeders, and the like. While such devices may be capable of metering a freely flowing powder when the output is averaged over a long period, short duration feed rates vary considerably, and they are unsatisfactory for applications requiring flow rates that are substantially steady and controllable over relatively short periods. In addition, with the exception of the rotary turntable feeder, such devices require a minimum of several grams of powder to operate which rules them out for use where only minute quantities are to be tested. While the rotary turntable feeder is capable of operating with quantities of powder in the milligram range, an operator must ensure that the powder is uniformly spread out over the turntable in order for the device to perform satisfactorily.

These and other problems are addressed, at least in part, by embodiments of the present invention which provide for the delivery of a powder aerosol at a stable and controllable rate suitable for short duration applications. While it is anticipated that embodiments of the present invention will find use in a variety of applications where controlled delivery of a powder aerosol is needed without departing from the spirit and scope of the invention, the embodiments illustrated below may be used in performing short duration inhalation toxicology studies of extremely toxic aerosol powers.

SUMMARY

In general, in one aspect, a system for delivering a powder aerosol includes an aerosol generator for atomizing a powder, a holding chamber into which the atomized powder is infused to form a concentrated aerosol cloud, a means for reducing the volume of the holding chamber and thereby expelling the concentrated aerosol at a controlled rate from an outlet port of the holding chamber, a source of gas for mixing with the concentrated powder aerosol expelled from the holding chamber, and a monitoring device to monitor the admixture of gas and concentrated aerosol to achieve a target aerosol concentration.

In general, in another aspect, a method for producing a substantially constant mass flow rate of a powder aerosol over a brief period includes infusing a powder aerosol into a holding chamber to form a concentrated aerosol cloud within the holding chamber, reducing the volume of the holding chamber to expel powder aerosol from an outlet port, mixing the powder aerosol expelled from the outlet port with a gas and monitoring the mass concentration of the admixture of gas and aerosol to achieve a target aerosol concentration.

DETAILED DESCRIPTION

In the following detailed description, reference is made to the accompanying drawings that form a part hereof, and in which are shown by way of illustration specific embodiments in which the invention, as claimed, may be practiced. This invention may, however, be embodied in many different forms and should not be construed as limited to the embodiments set forth; rather, these embodiments are provided so that this disclosure will be thorough and complete, and will fully convey the scope of the invention to those skilled in the art. As will be appreciated by those of skill in the art, the present invention may be embodied in methods, systems and devices. Wherever possible, the same reference numbers will be used throughout the drawings to refer to the same or like parts.

Embodiments according to the present invention provide systems and methods for the controlled generation of aerosols from small quantities of dry powder materials (between approximately 25-500 mg) and may be used in the conduct of short duration inhalation toxicology studies. Consistent and repeatable short duration aerosol feed rates are obtainable in embodiments according to the present invention. As will be seen, such approaches provide a simple, efficient, controllable and consistent dry aerosol delivery system suitable for a wide variety of inhalation studies. In the discussion that follows, embodiments of systems according to the present invention will be described first, followed by an explanation of their operation.

Figure 1:
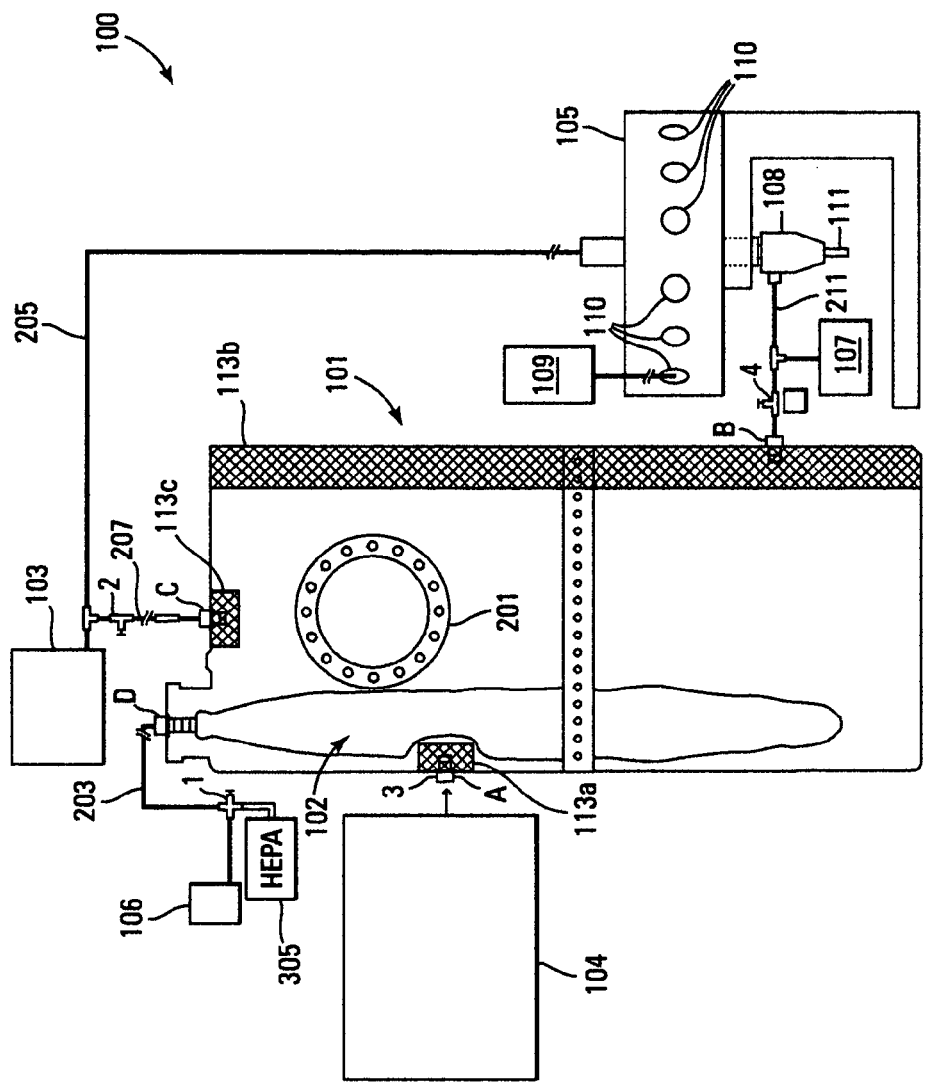
FIG. 1 is a simplified partial schematic profile view of a preferred embodiment of a system for delivering a powder aerosol according to the present invention.

FIG. 1 shows a simplified partial schematic profile view of a preferred embodiment of a powder aerosol delivery system 100 according to the present invention. Experiments involving toxic chemical or biological materials must, of course, be conducted within an appropriate containment device. For tests involving extremely toxic powder aerosols, system 100 may be housed within a multi-compartment glove box enclosure (Class III hood line) that is equipped with special provisions for transfer and decontamination of materials and equipment. Personal protective gear such as NBC respirators, positive pressure suits, and the like, may also be worn by lab personnel as may be appropriate.

System 100 is divided into two main compartments: an aerosol holding chamber 101 and a test chamber 105. Aerosol holding chamber 101 provides an atmospherically sealed enclosure into which a test powder is disseminated to form a concentrated aerosol cloud. Advantageously, the flow rate of test powder into the holding chamber need not be carefully metered. All that is needed is an infusion of a sufficient quantity of free flowing powder to form an aerosol cloud in holding chamber 101 that is somewhat more concentrated than the target aerosol concentration. A concentration that is approximately an order of magnitude greater than the concentration of aerosol to be supplied to test chamber 105 was found to be optimal in tests. As embodied herein, holding chamber 101 is made from a polycarbonate carboy rectangular enclosure that is approximately 25 liters in volume and dimensioned generally to be about three times taller than it is wide. Although sedimentation is generally not a serious problem with very small particles in short duration tests, where particle size and/or test duration make sedimentation more likely, a taller holding chamber 101 will allow one to maintain the aerosol suspended for a longer period of time in the holding chamber. Other embodiments may, of course, employ larger or smaller holding chambers of different shapes and sizes and other suitable materials may be used in constructing the holding chamber.

Figure 2:
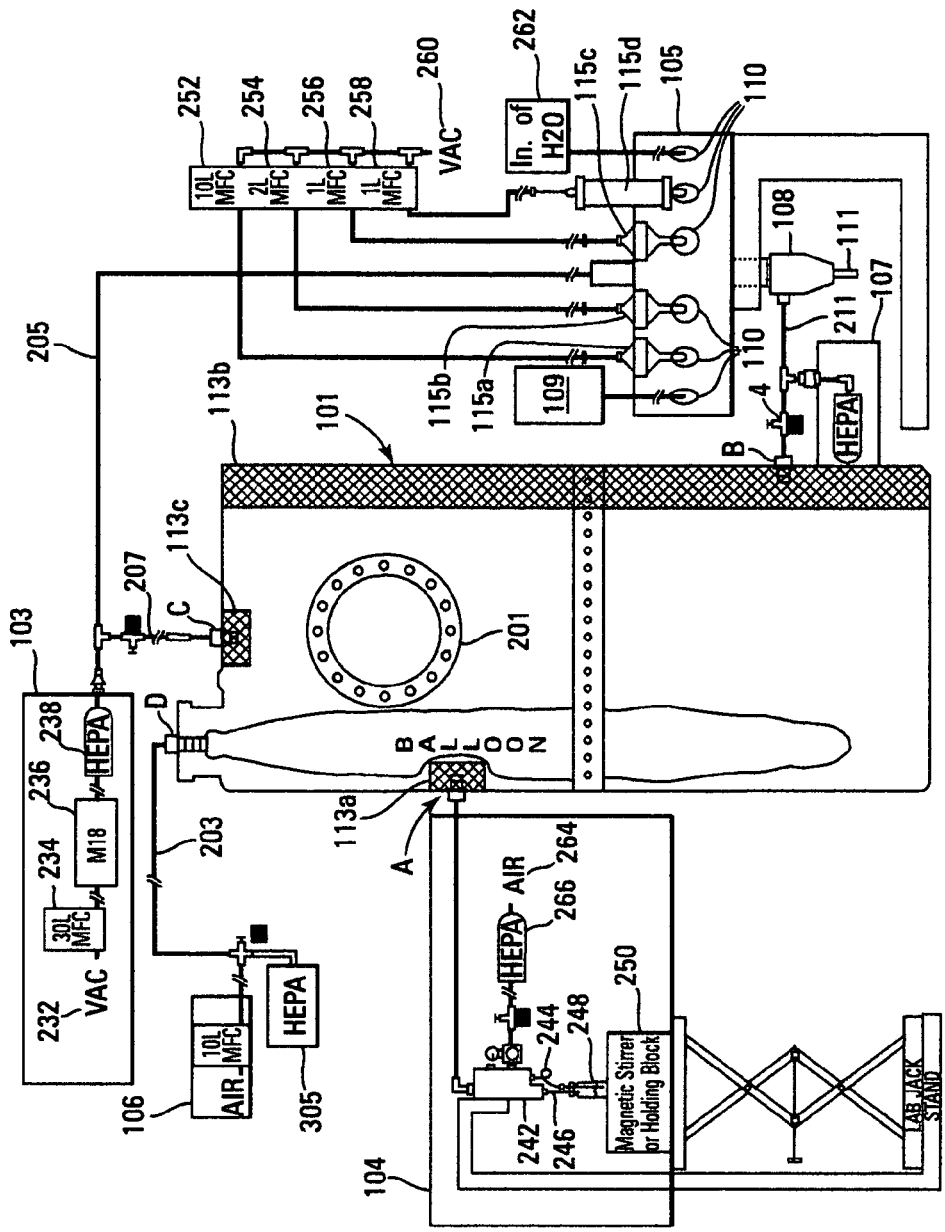
FIG. 2 is a partial schematic profile view of an embodiment of a system for delivering a powder aerosol according to the present invention showing one example of a powder aerosol generator.
Figure 3:
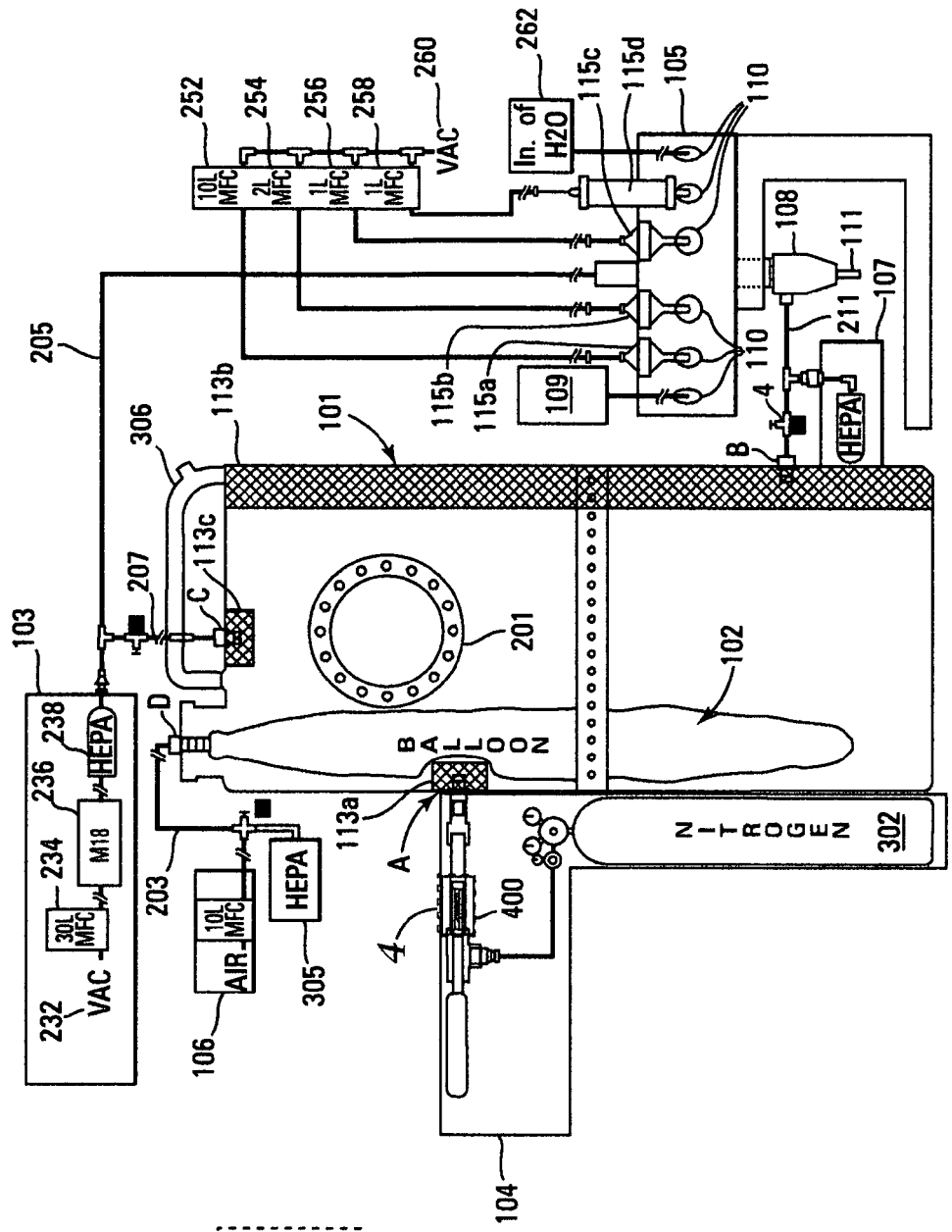
FIG. 3 is a partial schematic profile view of an embodiment of a system for delivering a powder aerosol according to the present invention showing another example of a powder aerosol generator.
Figure 4:
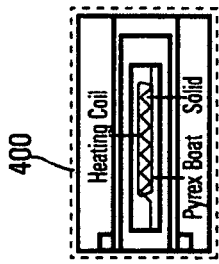
FIG. 4 is an enlarged view of the powder aerosol generator of FIG. 3.

Holding chamber 101 includes a number of openings or ports which provide atmospherically sealed inlets and outlets for flows of gas and aerosol conveyed through conduits attached externally to the ports. Ports A, B, C and D are shown in FIGS. 1-3. Manually or automatically actuated valves regulate the flow through the various conduits. Valves 1, 2, 3, and 4 are illustrated in FIGS. 1-3. To cause aerosol to be expelled from holding chamber 101 at a steady rate, the volume of aerosol holding chamber 101 is steadily reduced. There are several ways to accomplish this. Holding chamber 101 may be made from a flexible material that inflates as aerosol is introduced into the chamber and collapses as the aerosol is allowed to escape. Alternatively, holding chamber 101 may be made from a flexible material or be made collapsible like a bellows, and holding chamber 101 may be collapsed by applying force to one or more surfaces externally, such as by increasing the ambient atmospheric pressure surrounding holding chamber 101.

Perhaps the simplest way to change the volume of holding chamber 101, and the method preferred herein, is to displace the volume from within by inflating a cavity such as a bag or balloon positioned inside the chamber. As illustrated in FIGS. 1-3, a balloon 102 is provided inside holding chamber 101 and is sealingly attached internally to port D so that the balloon may be inflated or deflated without diluting the concentration of the aerosol within the holding chamber 101. Balloon 102 is dimensioned so that it displaces very little volume within holding chamber 101 when it is deflated but is preferably large enough to substantially fill the inner volume of holding chamber 101 upon inflation and still remain in a semi-flaccid state (i.e., not stretched to near capacity) so that only a slight positive pressure is required to maintain inflation. Balloon 102, as embodied herein, is a Mylar weather balloon but may also be implemented using a variety of expandable bladders, bags, bellows, or the like. An observation port 201 is shown in a sidewall of holding chamber 101 and may be useful in some applications to view the state of inflation of balloon 102 and the concentrated aerosol cloud.

Thorough clean up is necessary following an experiment involving a highly toxic substance. It is a time consuming and tedious process. Lab equipment such as vessels, conduits and enclosures which may have been used to mix and measure toxic materials must now be thoroughly decontaminated. The containment facility for the experiment may also require extensive decontamination and clean up if toxic powder is disseminated. Embodiments according to the present invention greatly simplify the clean up process by providing a system that is capable of metering and dispensing a powder aerosol directly from the vessel in which it has been stored and by providing a holding chamber 101 that is disposable. Ports A, B, C and D preferably provide pneumatic or air tight seals and are equipped with quick release fittings or the like to facilitate safe removal of the external conduits. Holding chamber 101 and balloon 102 are preferably manufactured from materials that facilitate safe dismantling and disposal. As shown in FIG. 3 holding chamber 101 may be equipped with a carrying handle 306 to facilitate handling.

A conduit 203 is attached externally to port D and connects balloon 102 to valve 1. Valve 1 is preferably a three-way valve that selects between an inflow to port D provided through a mass flow controller (MFC) 106 which supplies positive pressure to inflate the balloon and a HEPA filtered vent 305 which enables the balloon to be deflated by porting to the outside. As balloon 102 nears maximum inflation it may impede the flow through Ports A, B, and C. Screens or mesh covers 113a, 113b and 113c are placed over the inside openings of ports A, B and C to prevent the balloon 102 from impeding the flow after it has expanded within the chamber.

System 100 also includes an aerosol generator 104 which delivers a flow of aerosolized powder to holding chamber 101 at port A and is controllable by valve 3. Any one of a number of conventional devices may be used to generate the desired aerosol since, as noted, embodiments of the present invention do not rely on the aerosol generator to achieve the target mass concentration of the aerosol. Preferably, the aerosol generator is capable of dispersing a sufficient quantity of test material to fill holding chamber 101 with a concentrated aerosol. As noted, a concentration that is somewhat higher than the target aerosol concentration is generally desirable. An excessively concentrated aerosol, however, will result in excessive particle collisions and coagulation and should be avoided.

As illustrated in the embodiment shown in FIG. 2, aerosol generator 104 may be implemented using a conventional laboratory atomizer. In this example, atomizer 242 is a TSI, Incorporated Model 3076 designed for generation of liquid aerosols but also capable of dispersing a free flowing powder. In general, atomizer 242 should be able to deliver a quantity of powder appropriate for the material to be tested. The model 3076 operates at flow rates in the range of 1 to 3 liters per minute. Initial lab tests performed with a small sample of powder demonstrated that a free flowing powder aerosol in excess of 200 mg/m3 may be generated for several minutes. Atomizer 242 includes feed and return lines 244 and 246, respectively, which are fitted with hypodermic needles to pass through a septum cap or the like of a feed vessel 248. As shown in FIG. 2, a loop is provided in feed line 244, which helps prevent coagulation of powder. Advantageously, the same container such as a septum vial used to store the test powder may be employed as the feed vessel 248 thus eliminating the risks and inconvenience involved in transferring test materials from one container to another. Atomizer 242 is driven by a compressed air source 264 coupled through HEPA filter 266 and shutoff valve 3. To further facilitate aspiration, the powder may be agitated within feed vessel 248 by a magnetic stirrer 250, shown beneath.

Valve 4 opens and closes the outflow from port B of holding chamber 101 through conduit 211 and is mixed with make up air source 107 and a particle separator 108. Make up air source 107 is mixed with the concentrated aerosol output from port B of holding chamber 101. Particle separator 108 is connected to conduit 211 and is configured to remove particles that are larger than desired for the test before discharging the aerosol to test chamber 105. Oversize particles are discharged into a collection pot 111 for safe disposal later. In the illustrated embodiments, particle separator 108 is implemented using a cyclone separator and separates particles after the aerosol is discharged from the holding chamber, however, particle separation could be performed at an earlier or later stage of the process.

The second main compartment of system 100 is test chamber 105. Test chamber 105 is a manifold that receives the test aerosol outflow from cyclone 108 which is essentially at the target test concentration and distributes test aerosol to one or more exposure ports 110. In the illustrated embodiments, test chamber 105 has been implemented using a multi-port rodent nose-only inhalation exposure chamber. Sample filter holders 115a, 115b, and 115c, a cascade impaction particle sizing device 115d and an aerosol monitor 109 are shown attached to several exposure ports 110 of test chamber 105. Other ports 110 may be attached to compartments containing test animals.

Aerosol monitor 109 continuously and directly samples the admixture of aerosol and make up air from a test chamber exposure port 110 and analyzes the sample to determine whether the particle mass concentration in the test chamber is on target. Aerosol monitor 109 outputs data, essentially in real time, which may be used by an operator or an appropriate control system to maintain the target aerosol concentration throughout the test. Aerosol monitor 109 preferably is a laser light-scattering photometer and includes an optical scattering cell that has appropriate sensitivity for monitoring aerosols in the 0.5 to 2 microgram range (or other range of interest) such as a DUSTTRAK™ Aerosol Monitor manufactured by TSI Incorporated, or similar device. By varying the rate of inflation of balloon 102 in response to data from aerosol monitor 109 a high degree of precision in aerosol concentration provided to the test chamber 105 may be obtained.

While an operator may monitor and control the tests conducted with system 100, tests may also be automated using computer-based feedback control in response to data obtained from sensors including the aerosol mass monitor 109 in order to provide appropriate actuator signals through the operating stages of the system described below. Such an automated controller may be implemented using commercially available laboratory software such as Labview® and appropriate signal I/O hardware.

In general, the sum of the outflows from the test chamber 105 will determine the operating flow through the test chamber 105. Operating flow is closely monitored to ensure that aerosol is delivered to the test chamber at the appropriate rate. Additionally, in the illustrated embodiments operating flow controls the particle size allowed to pass through cyclone 108.

Inflow to the test chamber 105 is make up air drawn through HEPA filter 107 mixed with the concentrated aerosol from port B of holding chamber 101. Several vacuum sources generate outflows through test chamber 105. Vacuum source 260 is coupled to test chamber 105 through mass flow controllers (MFCs) 252, 254, 256 and 258 which regulate flows through test containers or tubes 115a, 115b, 115c and 115d. Dust Trak 109 also includes its own filtered vacuum source which provides a flow sufficient to monitor the aerosol concentration in test chamber 105. A main system exhaust control 103 is connected to test chamber 105 by conduit 205 and provides filtering, monitoring and regulating of the exhaust flow from test chamber 105. As shown in FIG. 2, main system exhaust control 103 includes a vacuum (VAC) source 232 coupled to a 30 liter MFC 236 to regulate the main exhaust vacuum, a carbon filter M18 236 (to remove any vapor contaminants from the exhaust that might be present), followed by a high efficiency particulate air filter (HEPA) 238. Valve 2 (which is normally closed during a test) controls the flow through conduit 207 which connects port C of holding chamber 101 to conduit 205 so that pressure can be equalized between test chamber 105 and holding chamber 101. Atmospheric pressure in test chamber 105 is monitored by a barometric sensor 262. Generally, the pressure should be slightly negative relative to ambient air pressure to make sure there is no leakage from test chamber 105 to the outside.

FIG. 3 shows an alternative embodiment of the present invention in which the powder aerosol is generated by electrothermal vaporization using a thermal vapor generator 400 such as a Pyro-probe, or the like. In this system, an inert, non-reactive processing gas 302 such as nitrogen or argon flows across the pyro-probe at ambient temperature causing the vapor to condense into a concentrated aerosol stream that flows to port A of holding chamber 101.

In some embodiments, in the outflow from aerosol generator 104 an accumulation of charge may cause particles to adhere to surfaces of conduits and chambers. Excessive charge can be neutralized by passing particles through an ion neutralizer such as a Thermo-Systems, Inc. Krypton-85 2 milicurie source, a corona discharge device or an ion source, or the like. Such devices are readily available and are generally effective at removing excess charge. Appropriate sensors and controllers may be employed to monitor and control electrostatic levels, humidity, temperature, gas pressure and concentration and other environmental variables, to maintain the proper experimental environment, as would be familiar to those of skill in the art.

Operation of a preferred embodiment of a system according to the present invention will now be described. In general, there are three main stages of operation: the balloon inflation stage, the aerosol filling stage and the controlled dissemination stage.

Balloon Inflation Stage

In this first stage, balloon 102 is inflated to fill the interior volume of the holding chamber 101. This is accomplished by positioning valve 1, preferably, a 3-way type valve, in the vent position (i.e., the inner volume of the balloon is vented to the outside). Valve 2, which connects holding chamber 101 to the main system exhaust control 103, is opened. Valves 3 and 4 are closed during this operation. As gas is drawn from chamber 101 by main system exhaust control 103, balloon 102 is caused to inflate. When full inflation is reached, valve 2 is closed while valve 1 remains in the vent position. Stage two of the operation, the aerosol filling phase, is now ready to commence.

Aerosol Filling Stage

The aerosol filling stage begins by opening valve 3 at aerosol fill port A to enable the flow from aerosol generator 104 to pass into holding chamber 101. Since balloon 102 is initially in the fully inflated position in this stage, aerosol flowing into port A will begin to force air out of port D and gradually collapse the balloon. Since the fill rate and box volume are known with prior experience, the operator can determine when the chamber is completely full and the balloon is collapsed by timing this stage. Additionally, the operator may be able to observe the inflation state of the balloon through observation port 201, if one is provided. By filling holding chamber 101 in this fashion, embodiments of the present invention effectively avoid the problem of mixing the incoming aerosol with clean air in the holding chamber and undesirably diluting the resulting aerosol concentration. Infusion of aerosol into holding chamber 101 is allowed to continue until balloon 102 is substantially collapsed. Additional air may be added to completely fill the box if the test powder has already been exhausted.

After balloon 102 has completely collapsed, valve 3 at port A is closed to stop the flow from aerosol generator 104 into holding chamber 101 and valve 1 is positioned to close the vent and to connect port D to the balloon MFC 106. The holding chamber 101 is now primed with aerosol and stage three, the controlled dissemination stage can begin.

Controlled Dissemination Stage

The controlled dissemination stage begins by equalizing the pressure in holding chamber 101 with the pressure in the test chamber 105. This is accomplished by opening valve 2 for about 10 seconds and is done to prevent a sudden uncontrolled surge of aerosol into the test chamber when valve 4 is first opened. After the pressure has equalized, valve 2 is closed.

Controlled dissemination is initiated by opening valve 4 and immediately starting the MFC 106 which initiates a flow at a minimum preset value to fill the balloon. As the balloon inflates at a controlled rate, concentrated aerosol is forced out of the holding chamber 101 via port B which then mixes with particle free makeup air from chamber filtered air source 107. Together, the two flows add up to the total chamber flow. The resulting concentration of aerosol in the test chamber 105 is, in effect, determined by the mixing ratio of aerosol flow from the holding chamber and the particle free make up air stream. This diluted aerosol stream then passes through cyclone separator 108 prior to entering the test chamber. Cyclone separator 108 limits the size of aerosol particles reaching test chamber 105 thereby stabilizing the aerosol particle size distribution in the test chamber over the time course of the test. As the diluted aerosol stream flows through the test chamber, its mass concentration is continuously measured using optical aerosol monitor 109. Feedback from the optical aerosol monitor 109 is used to maintain the target aerosol concentration by appropriately varying the balloon inflation rate. Using this approach, it is possible to achieve well regulated (+/10% of the mean or lower) aerosol concentration levels over a wide range of aerosol concentrations (of at least 0.1 to 50 mg/m3 of air).

CONCLUSION

As has been shown, embodiments of the present invention safely and accurately provide for the controlled generation and delivery of aerosols from small quantities of powder for short duration inhalation toxicology studies. A number of embodiments of the invention defined by the following claims have been described. Nevertheless, it will be understood that various modifications to the described embodiments may be made without departing from the spirit and scope of the claimed invention. For example, while the present invention was designed specifically for short duration testing of highly toxic airborne particulates, those of ordinary skill in the art will recognize that embodiments may be employed for testing a wide variety of toxic and non-toxic airborne particulates, particularly for short duration tests with fine particulate aerosols including vehicle exhaust emissions, industrial emission sources, soil, volcanic dust, road dust, dust resulting from other human activities (i.e. agriculture), smoke from forest fires, smoke from recreational sources (i.e. campfires and fireplaces). In addition, embodiments of the present invention may be adapted for use with radioactive particulates by providing appropriate shielding. Various process stages may also be performed in a different order from the embodiments described herein, as would be apparent to those of skill in the art. Accordingly, other embodiments are within the scope of the invention, which is limited only by the following claims.

What is claimed is:

1. A system for delivering a powder aerosol, comprising:
   an aerosol generator for atomizing a powder;
   a holding chamber into which the atomized power is infused to form a concentrated aerosol cloud;
   means for reducing the volume of the holding chamber and thereby expelling the concentrated aerosol at a controlled rate from an outlet port of the holding chamber;
   a source of gas for mixing with the concentrated powder aerosol expelled from the holding chamber; and
   a monitoring device to monitor the admixture of gas and concentrated aerosol to achieve a target aerosol concentration.

2. The system for delivering a powder aerosol of claim 1, wherein the means for reducing the volume of the holding chamber comprises an expandable bag positioned within the holding chamber.

3. The system for delivering a powder aerosol of claim 2, wherein the expandable bag comprises a balloon.

4. The system for delivering a powder aerosol of claim 1, further comprising a manifold coupled to the outlet port of the holding chamber, the manifold comprising a plurality of test ports.

5. The system for delivering a powder aerosol of claim 4, further comprising a particle separator to regulate the size of particles comprising the powder aerosol.

6. The system for delivering a powder aerosol of claim 5, wherein the particle separator comprises a cyclone separator.

7. The system for delivering a powder aerosol of claim 4, wherein the manifold comprises a multi-port inhalation exposure chamber.

8. The system for delivering a powder aerosol of claim 7, further comprising a container for holding a test subject coupled to a port of the multi-port inhalation exposure chamber.

9. The system for delivering a powder aerosol of claim 1, further comprising a containment device for preventing dissemination of toxic aerosol.

10. The system for delivering a powder aerosol of claim 8, further comprising a vacuum source to facilitate flow through the multi-port inhalation exposure chamber.

11. The system for delivering a powder aerosol of claim 1, wherein the monitoring device comprises a laser light-scattering photometer that includes an optical scattering cell.

12. The system for delivering a powder aerosol of claim 1, wherein the monitoring device provides substantially real-time data to regulate the target aerosol concentration.

13. A method for producing a substantially constant mass flow rate of a powder aerosol over a relatively brief period, said method comprising:
   infusing a powder aerosol into a holding chamber to form a concentrated aerosol cloud therein;
   reducing the volume of the holding chamber to expel powder aerosol from an outlet port;
   mixing the power aerosol expelled from the outlet port with a gas; and
   monitoring the mass concentration of the admixture of gas and aerosol to achieve a target aerosol concentration.

14. A system for delivering a powder aerosol, comprising:
   means for generating a powder aerosol;
   means for holding a concentrated volume of powder aerosol coupled to the means for generating the powder aerosol;
   means for reducing the volume contained within the means for holding the concentrated volume of powder aerosol so as to expel concentrated powder aerosol;
   means for controlling the rate at which the concentrated powder aerosol is expelled;
   means for mixing the concentrated powder aerosol with a gas to achieve a target powder aerosol concentration; and
   means for monitoring the admixture of aerosol concentration and gas to maintain the target powder aerosol concentration.

15. A system for delivering an aerosol, comprising:
   an aerosol holding chamber comprising an inlet port, an exhaust port, a bag port and an outlet port;
   a bag positioned within the aerosol holding chamber and pneumatically coupled to the bag port;
   a source of gas for inflating the bag;
   a controller for deflating the bag at a predetermined rate;
   an aerosol generator pneumatically coupled to the inlet port of the aerosol holding chamber;
   a test chamber comprising one or more test ports coupled to the outlet port of the aerosol holding chamber;
   a particle separator to limit the size of particles reaching the test chamber;
   a source of gas coupled to the outlet port of the aerosol holding chamber; and
   a monitoring device coupled to a test port of the test chamber;
   wherein concentration of the aerosol provided to the test chamber may be monitored and regulated.

16. The system for delivering a powder aerosol of claim 15, wherein the particle separator comprises a cyclone separator.

17. The system for delivering an aerosol of claim 15, wherein the test chamber comprises a multi-port inhalation exposure chamber.

18. The system for delivering an aerosol of claim 17, further comprising a container for holding a test subject coupled to a port exposure chamber.

19. The system for delivering an aerosol of claim 15, further comprising a glove box enclosure.

20. The system for delivering an aerosol of claim 15, further comprising a vacuum source to generate outflow from the test chamber.

21. The system for delivering an aerosol of claim 15, wherein the particle separator comprises a cyclone separator.

22. The system for delivering an aerosol of claim 15, wherein the monitoring device comprises a laser light-scattering photometer that includes an optical scattering cell.

23. A method for producing a substantially constant mass flow rate of a powder aerosol over a relatively brief period, the method, comprising:
   providing a sealable aerosol holding chamber comprising an inflatable bag positioned therein;
   inflating the bag to cause gas within the holding chamber to be displaced and to be exhausted from an opening in the holding chamber;
   sealing the opening in the holding chamber after the bag has been inflated to a predetermined size;
   venting the inflated bag after it has reached the predetermined size;
   infusing a powder aerosol into the holding chamber thereby causing the vented bag to deflate; and
   reinflating the bag at a controlled rate to cause powder aerosol to be output from an opening in the holding chamber.

24. The method of claim 23, further comprising mixing the powder aerosol output from the holding chamber with a gas to dilute the powder aerosol to a target concentration.

25. The method of claim 24, further comprising separating particles above a predetermined size from the powder aerosol.

26. The method of claim 23, further comprising monitoring the mass concentration of aerosol output from the holding chamber to achieve a target output aerosol concentration.

27. The method of claim 23, further comprising providing the powder aerosol output from the holding chamber to a test chamber.

* * * * *